United States Patent
Leiboff (10) Patent No.: US 8,216,159 B1
(45) Date of Patent: Jul. 10, 2012

(54) ANASTOMOSIS LEAK TESTING APPARATUS AND METHODS

(75) Inventor: Arnold R. Leiboff, Stony Brook, NY (US)

(73) Assignee: Tools For Surgery, LLC, Stony Brook, NY (US)

( * ) Notice: Subject to any disclaimer, the term of this patent is extended or adjusted under 35 U.S.C. 154(b) by 527 days.

(21) Appl. No.: 12/247,257

(22) Filed: Oct. 8, 2008

Related U.S. Application Data (60) Provisional application No. 60/978,176, filed on Oct. 8, 2007, provisional application No. 61/051,847, filed on May 9, 2008.

(51) Int. Cl.
*A61B 5/103* (2006.01)
*A61B 5/117* (2006.01)
*A61B 5/00* (2006.01)
*A61M 31/00* (2006.01)
*A61M 37/00* (2006.01)

(52) U.S. Cl. .......... 600/593; 604/26; 600/560; 600/561; 600/587

(58) Field of Classification Search .......... 600/561, 600/587, 593
See application file for complete search history.

(56) References Cited

U.S. PATENT DOCUMENTS

| | | | | |
|---|---|---|---|---|
| 464,692 | A | | 12/1891 | Crane |
| 2,428,483 | A | * | 10/1947 | Wittenberg ............ 137/493 |
| 2,906,282 | A | * | 9/1959 | Shannon ............... 137/228 |
| 2,954,751 | A | * | 10/1960 | Barnes, Jr. ............ 116/268 |
| 3,011,470 | A | * | 12/1961 | Stoermer ............. 116/268 |
| 3,800,586 | A | * | 4/1974 | Delatorre et al. ........ 73/49.2 |
| 4,029,042 | A | * | 6/1977 | Juhasz ................ 116/267 |
| 4,971,034 | A | | 11/1990 | Doi et al. |
| 5,047,010 | A | | 9/1991 | Ams et al. |
| 5,616,157 | A | * | 4/1997 | Mead et al. ............. 96/421 |
| 6,056,699 | A | | 5/2000 | Sohn et al. |
| 6,402,688 | B1 | | 6/2002 | Takami et al. |

(Continued)

FOREIGN PATENT DOCUMENTS

WO 2005065075 7/2005

OTHER PUBLICATIONS

International Search Report for International App. No. PCT/US04/30047 which corresponds to U.S. Appl. No. 10/664,366 which published as 20050059992.

(Continued)

*Primary Examiner* — Max Hindenburg
*Assistant Examiner* — Adam Eiseman
(74) *Attorney, Agent, or Firm* — Brian Roffe (57) ABSTRACT

Anastomosis leak testers for testing for leaks in gastrointestinal anastomoses in patients include an inflation pump and a conduit part. The inflation pump has a compressible portion and a mechanism for providing a uni-directional flow of air through the inflation pump upon intermittent compressing thereof. Conduit parts have an interior space, a portion to be inserted into an anus of a patient or arm to be mated to a gastric tube, rectal tube or endoscope, a pressure relief valve and an indicator pin, and a rearward arm connected to the inflation pump. Upon actuation of the inflation pump, air flows through the inflation pump and through the conduit part into the patient's bowel. When the air pressure in the bowel exceeds a specified pressure, air is released through the pressure relief valve and ejects the indicator pin, which alerts the surgeon that the desired rectal pressure has been reached.

16 Claims, 3 Drawing Sheets

U.S. PATENT DOCUMENTS

| | | |
|---|---|---|
| 6,451,029 B1 | 9/2002 | Yeatman |
| 6,503,259 B2 * | 1/2003 | Huxel et al. .................. 606/153 |
| 6,585,662 B1 | 7/2003 | Jones et al. |
| 2005/0059992 A1 | 3/2005 | Leiboff |
| 2006/0217637 A1 | 9/2006 | Leiboff et al. |
| 2008/0004566 A1 * | 1/2008 | Sloan .............................. 604/30 |

OTHER PUBLICATIONS

Written Opinion for International App. No. PCT/US04/30047 which corresponds to U.S. Appl. No. 10/664,366 which published as 20050059992.

* cited by examiner

ANASTOMOSIS LEAK TESTING APPARATUS AND METHODS

CROSS REFERENCE TO RELATED APPLICATIONS

This application claims priority under 35 U.S.C. §119(e) of U.S. provisional patent application Ser. Nos. 60/978,176 filed Oct. 8, 2007 and 61/051,847 filed May 9, 2008, which are incorporated by reference herein.

FIELD OF THE INVENTION

The present invention relates to anastomosis leak testing apparatus for introducing air into the rectum or stomach of a patient during a surgical operation in order to evaluate the integrity of an anastomosis.

BACKGROUND OF THE INVENTION

Surgical operations to remove the distal colon and part of the rectum are common for illnesses such as neoplasia, diverticular disease and inflammatory bowel disease. When the continuity of the intestinal tract is to be preserved, the bowel must be reconnected, for example, by means of sutures, staples or a compression device. This connection is called an anastomosis.

If there is a defect in the anastomosis, bowel content can leak out of the bowel and contaminate the normally sterile peritoneal cavity, causing peritonitis. Peritonitis (infection of the peritoneal cavity) can be lethal, and, therefore, measures must be taken during surgery to ensure that defects in the anastomosis are not present. One such measure is to fill the pelvic portion of the abdominal cavity with saline or water to a level that immerses the completed anastomosis, then insufflate the rectum with air while occluding the bowel above the anastomosis. As the rectum distends, the pool of saline is observed for air bubbles that, if present, signal a defect in the anastomosis, i.e., a leak, which must then be repaired.

One method currently used to insufflate the rectum is to insert a catheter into the rectum and, through the catheter, inject air into the rectum with a large syringe. The catheter may or may not have an inflatable retention cuff at its tip. A Foley catheter is a useful example of a catheter with an inflatable cuff that is readily available in an operating room. In this method, air is injected into the rectum through the catheter, the catheter is then clamped or crimped, the syringe is detached, refilled with air, reattached to the catheter, and more air is injected. This cycle is continued until the rectum is sufficiently distended with air. This method utilizes both a catheter and a syringe and is somewhat cumbersome.

A more frequently used device to insufflate air into the rectum and distend an anastomosis is a proctoscope, i.e., a rigid cylindrical instrument designed for looking into the rectum. A proctoscope, also referred to as a sigmoidoscope, is a type of endoscope. The proctoscope has a tubing port to which tubing from an insufflation bulb is attached. With the lens gate of the proctoscope closed, air is introduced into the rectum by compressing the insufflation bulb. Less frequently, flexible endoscopes, e.g. flexible sigmoidoscopes or colonoscopes, are used to inflate and inspect the anastomosis. Flexible endoscopes also have channels for air insufflation.

Use of a proctoscope for rectal insufflation to test for anastomotic leaks has advantages and disadvantages. The fact that proctoscopes are items usually stocked in an operating room is an advantage. Thus, an additional surgical instrument does not need be purchased or stocked in an operating room in order to test for anastomotic leaks. Moreover, it is advantageous that it is possible to visually inspect the anastomosis from inside the bowel using the proctoscope. This helps identify potentially harmful bleeding, which can then be stopped by suture ligation.

On the other hand, a significant disadvantage of the use of a proctoscope results from the fact that a sterile proctoscope has to be contaminated to check for leaks and then repackaged and sterilized for future use. The cost savings gained by using an instrument already in stock and accessible may be lost by the extra labor involved in cleansing, repackaging and sterilizing the instrument after surgery.

Another disadvantage is that if a proctoscope is used at the very start of surgery to examine a rectal tumor or cleanse the rectum, as is often done, then it must either be kept in the operating room in a dirty state, or cleansed in a nearby utility room by a nurse, until such time as it is again needed to test the anastomosis. This not only clutters the operating room, but can potentially contaminate the operating room, and in any event, necessitates extra labor, for example, by a circulating nurse.

An additional disadvantage of using a proctoscope to insufflate the rectum is that the insufflated air tends to leak out through the anus around the proctoscope, which typically has an outer diameter of about 0.75 inches. It therefore requires some extra effort to distend the rectum to the desired amount to effectively test the anastomosis. This problem is accentuated when the anastomosis is at or near the anus. When the anastomosis is very low, it may be impossible to inflate the anastomosis to the desired pressure.

Another disadvantage of using a proctoscope or other endoscope, or catheter, is that these instruments do not provide a mechanism to signal the surgeon when a specified air pressure is reached, and thus the air pressure can only be grossly evaluated by visual inspection of the distended bowel above the pool of saline, or by feeling the bowel. An anastomosis my therefore be under-inflated, in which case an anastomotic defect might go unrecognized.

Another disadvantage of using a proctoscope or other endoscope, or catheter, is that these instruments do not provide a mechanism to prevent overinflation, which may possibly damage or disrupt an anastomosis.

Furthermore, before performing an anastomosis some surgeons prefer to cleanse the bowel with an antiseptic. If a proctoscope that was used earlier to view a tumor or cleanse the rectum is reused to test an anastomosis without being resterilized, then the rectum will be insufflated with particles of fecal debris or airborne bacteria that remain within the scope or within the insufflation bulb or tubing that carries air from the insufflation bulb to the proctoscope. Such fecal debris or airborne bacteria could contribute to the development of postoperative peritonitis or wound infection when forced through an anastomotic defect into the sterile peritoneal cavity.

Thus, there are significant drawbacks to the use of a standard proctoscope to insufflate air into the rectum and to inspect an anastomosis and it would be desirable to provide alternative means to insufflate the rectum and inspect the anastomosis that avoid these drawbacks.

Operations of the upper intestinal tract also may require the formation of an anastomosis. For example, "gastric bypass" is a commonly performed operation on the morbidly obese that has been shown to produce significant weight loss. In this operation, a gastroenteric anastomosis is formed between a portion of the stomach and the small bowel. Bariatric surgeons often test their gastric anastomoses by a method similar to that described above for a colorectal anastomosis. Thus, they insufflate air or a gas into the stomach by means of a tube passed through the mouth into the stomach (a gastric tube). They occlude the bowel beyond the anastomosis and immerse the anastomosis in clear fluid. If they see air bubbling out of the bowel, through the fluid, they know that they have a defective anastomosis and must repair it immediately.

The most common way the stomach is insufflated during surgery is by passing a gastroscope into the esophagus or stomach. A gastroscope is another type of flexible endoscope. Gastroscopes are routinely used for examining the stomach and are attached to air pumps that insufflate the organ through a channel in the scope. However, this requires the availability and preparation of the gastroscope, and also requires the surgeon to remove the gastric calibration tube often used in bariatric surgery. Another method is to inflate the anastomosis with gas (e.g., oxygen) by attaching an infusion line from the anesthesiologist's cart to the gastric calibration tube. Either method is somewhat cumbersome, and neither allows the surgeon to inflate to a standardized pressure, or to measure, determine or record the precise inflation pressure.

OBJECTS AND SUMMARY OF THE INVENTION

It is an object of some embodiments of the present invention to provide simple, inexpensive and disposable devices to be used during surgery for insufflation of the rectum or stomach with air to test for anastomotic leakage.

It is another object of some embodiments of the present invention to provide new methods for testing for gastrointestinal anastomotic leaks using novel anastomosis leak testers.

It is still another object of some embodiments of the present invention to provide anastomosis leak testers that are easier to use than endoscopes for the purpose of testing colorectal anastomoses for leaks.

It is yet another object of some embodiments of the present invention to provide anastomosis leak testers that are safer to use than endoscopes for the purpose of testing colorectal anastomoses for leaks.

It is another object of some embodiments of the invention to provide anastomosis leak testers that are useful for testing very low colorectal and coloanal anastomoses by occluding the anus at the anal verge.

It is still another object of some embodiments of the present invention to provide anastomosis leak testers that are easier to use than endoscopes for the purpose of testing gastric anastomoses for leaks.

It is yet another object of some embodiments of the present invention to provide anastomosis leak testers that are safer to use than endoscopes or than attaching gas lines to gastric tubes, for the purpose of testing gastric anastomoses for leaks.

It is another object of some embodiments of the present invention to provide anastomosis leak testers that prevent over-inflation of the bowel.

It is another object of some embodiments of the present invention to provide anastomosis leak testers that provide a signal when a predetermined air pressure within the rectum or stomach is reached.

It is another object of some embodiments of the present invention to provide anastomosis leak testers that provide palpable or visual signals when a predetermined intraluminal air pressure has been reached.

Still another object of some embodiments of the present invention is to provide inexpensive anastomosis leak testers that can lead to cost savings and more efficient use of operating room time and personnel.

In order to achieve at least one of these objects and possibly others, anastomosis leak testers for testing for leaks in anastomoses in patients in accordance with the invention include an inflation pump and conduit part. The inflation pump has a compressible portion and a mechanism for providing a uni-directional flow of air through the compressible portion upon intermittent compressing thereof. The conduit part has an interior space and an opening communicating with the interior space and adapted to be inserted into an anus of the patient or attached to a gastric tube, a pressure relief valve, a indicator pin and an aperture that allows air to escape the space between the valve and indicator pin. Upon compression of the inflation pump, air flows into the interior space of the conduit part and through the opening into the patient. When pressure in the patient's stomach or rectum exceeds a predetermined pressure, air flows through the pressure relief valve and ejects part of the indicator pin from the conduit part, e.g., a shaft of the indicator pin. The ejected part of the indicator pin is seen or felt by the surgeon, which signals that the desired pressure in the stomach or rectum has been reached. Ejection of the part of the indicator pin exposes an aperture in the conduit part between the valve and indicator pin through which air escapes when additional air is pumped into the interior space of the conduit part by further compressions of the inflation pump. This prevents pressure in the conduit part or bowel from exceeding the predetermined pressure no matter how rapidly or long air is pumped into the conduit part.

The conduit part of the anastomosis leak tester can have different forms. For example, it may be elongate, flexible, tubular, transparent and/or translucent. The opening of the conduit part through which air is discharged into the patient may be in line with the inflation pump or askew. A preferred embodiment of a colorectal anastomosis leak tester includes a conduit part with an opening for discharge of air into the rectum coaxial with the inflation pump. The conduit part of this preferred embodiment has a forward portion for insertion into the anus, an expanded portion for sealing the anal opening when pressed against the anal verge and for limiting insertion of the device into the anus, and a rearward portion, having a first arm for connecting with the inflation pump, and a second arm for housing the pressure relief valve and indicator pin.

A preferred embodiment of a gastrointestinal anastomosis leak tester has the pressure relief valve and indicator pin in line with the inflation pump. The conduit part of this preferred embodiment has a forward arm housing the indicator pin and pressure relief valve, a rearward arm connecting with the inflation pump, and a side arm with an opening constructed to mate with a tubing connector, for example, from a gastric tube.

An exemplifying method for colorectal anastomosis leak testing in accordance with the invention includes the steps of providing an anastomosis leak tester comprising an elongate elastomeric conduit part having an interior space, a forward portion having an opening communicating with the interior space and an expanded portion, a rearward portion containing a pressure relief valve and a movable indicator pin, and an inflation pump, inserting the forward portion of the conduit part into the anus of a patient to cause the expanded portion to seal the anal opening, filling the pelvis of the patient with fluid, occluding the bowel proximal to the anastomosis, compressing the inflation pump one or more times to cause air to flow through into the interior space of the conduit part and out of the opening into the rectum to thereby distend the rectum of the patient with air, and once the rectum is sufficiently distended, checking for anastomotic leaks based on the presence of air bubbles in the pelvic fluid. The surgeon continues to compress the inflation pump until he feels at least part of the indicator pin ejected from a lumen of the rearward portion of the conduit part. The anastomosis leak tester is then removed from the anus.

A colorectal anastomosis leak tester in accordance with the invention, and method for using the same, has several advantages over the prior art, notably the use of a standard proctoscope, or flexible endoscope, for the purpose of insufflating the rectum to test for anastomotic leakage. An anastomosis leak tester in accordance with the invention is easier to use than a proctoscope or flexible endoscope, because it is more compact and requires only one hand to operate, whereas a proctoscope, or flexible endoscope, is relatively unwieldy and requires two hands to use, one to position the proctoscope or endoscope and the second to operate the inflation mechanism. The device in accordance with the invention is also easier to use than a proctoscope because it prevents air from escaping from the rectum around the device, resulting in fewer inflation pump compressions to achieve the same rectal distension.

An anastomosis leak tester in accordance with the invention is also safer to use than a standard proctoscope, or flexible endoscope, because the device is always clean or sterile until used to insufflate the rectum and therefore no potentially hazardous debris collects in the device, nor is there a possibility of debris originating from the device contaminating the peritoneal cavity (as is the case when a contaminated scope is used.)

A gastrointestinal anastomosis leak tester in accordance with the invention, and method for using the same, has several advantages over the prior art, notably the use of a gastroscope or gas supply line for the purpose of insufflating the stomach to test for anastomotic leakage. An anastomosis leak tester in accordance with the invention is easier to use than a gastroscope because it is more compact and requires only one hand to operate, whereas a gastroscope is relatively unwieldy and requires two hands to use. An anastomosis leak tester in accordance with the invention also does not require the removal of the gastric calibration tube. Therefore, if a leak is detected, the anastomosis can be repaired with the gastric calibration tube in place, without having to remove or replace the tube.

The anastomosis leak testers in accordance with the invention are also designed to be inexpensive alternatives to proctoscopes or gastroscopes and to be easier to open, use and dispose of than it would be to cleanse or sterilize and repackage an endoscope.

The anastomosis leak testers in accordance with the invention are also safer to use, because they prevent the surgeon from injuring or disrupting an anastomosis by over-inflating the bowel by providing a pressure relief valve.

The anastomosis leak testers in accordance with the invention also provide a palpable or visual signal when a preferred air pressure within the bowel is reached, and thereby ensure that the anastomosis will be tested to a preferred and standardized pressure.

Some surgeons prefer the use of a proctoscope because it allows them to visualize the interior of a colorectal anastomosis and to check for anastomotic bleeding. An alternative use of the gastrointestinal anastomosis leak tester would be to replace the insufflation bulb and insufflation bulb tubing of a proctoscope. By attaching the arm with an opening constructed to mate with a tubing connector to the insufflation tubing port of the proctoscope, the gastrointestinal anastomosis leak tester can inflate the rectum to a desired pressure, signal the surgeon that the desired pressure has been reached, and prevent overinflation.

BRIEF DESCRIPTION OF THE DRAWINGS

The invention, together with further objects and advantages thereof, may best be understood by reference to the following description taken in conjunction with the accompanying drawings wherein like reference numerals identify like elements.

DETAILED DESCRIPTION OF THE INVENTION

Figure 1:
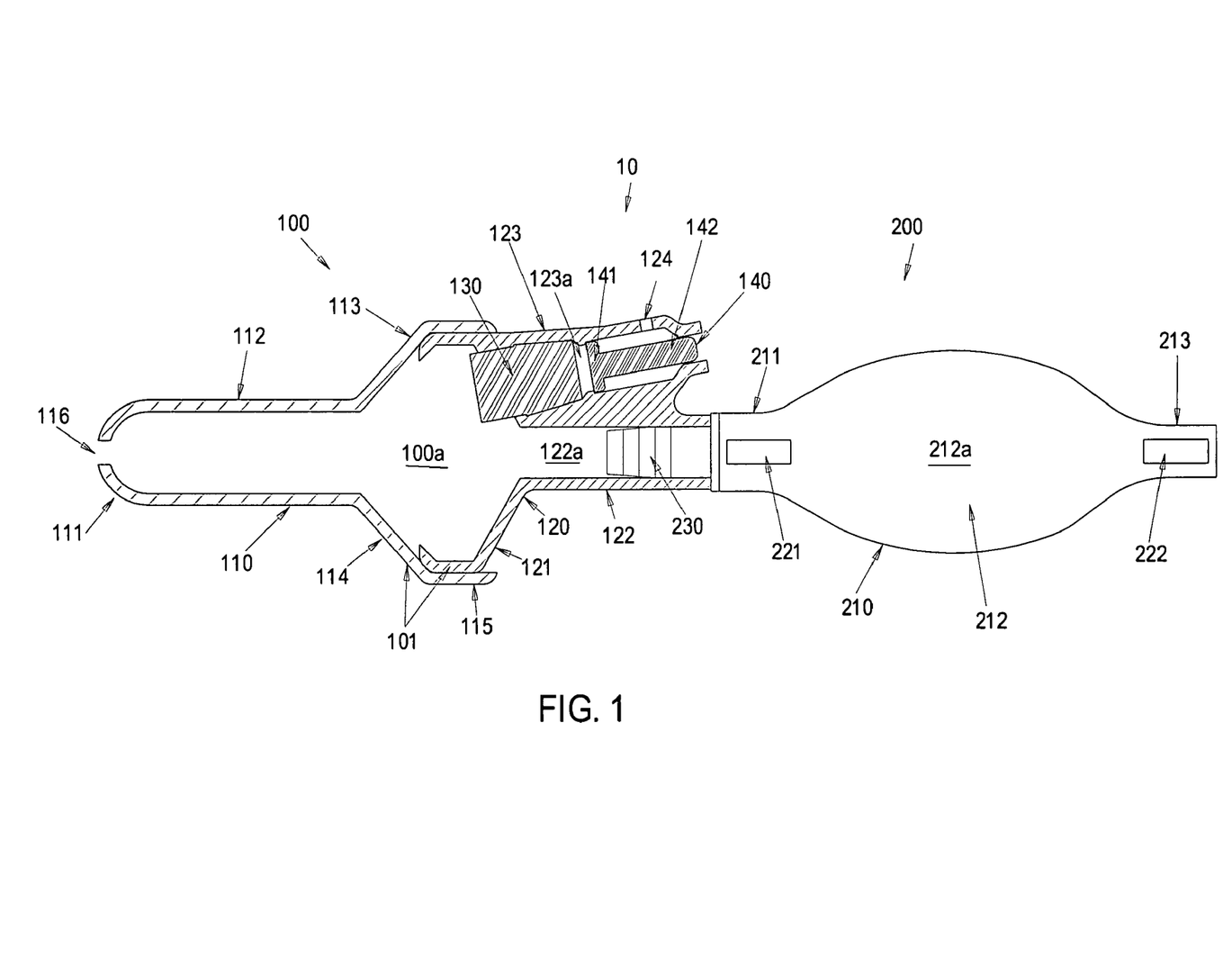
FIG. 1 is a partial longitudinal-section view of a colorectal anastomosis leak tester in accordance with the invention, with the indicator pin set inward in the unejected position.

Referring to the accompanying drawings wherein like reference numerals refer to the same or similar elements, FIG. 1 shows an embodiment of a colorectal anastomosis leak tester in accordance with the invention which is designated generally as 10. The anastomosis leak tester 10 comprises conduit part 100 and inflation pump 200. Conduit part 100 comprises body 101, pressure relief valve 130 and indicator (signal) pin 140.

Body 101, which defines interior space 100a of anastomosis leak tester 10, may be made of an elastomer compatible for contact with internal parts of the human body, namely the anal wall and anal opening as discussed below, and fabricated using a dip molding technique to obtain a soft, pliable form. Other plastic manufacturing methods can also be used.

Body 101 may be formed in two pieces 110 and 120, as shown in FIG. 1, a rearward portion 120 being insertable into and connected to a forward portion 110. These pieces may be dip molded or injected molded.

Forward portion 110 of body 101 has a tip 111, a cylindrical section 112 and an expanded section 113. Tip 111 is rounded or tapered to aid insertion of cylindrical section 112 into the anus of an anesthetized patient. Expanded section 113 has an outer circumferential lip 115 having the largest diameter of the entire body 101 and which is dimensioned to be larger than the opening of most human anuses when they are maximally dilated so that the conduit part 100 cannot be inserted into the anus farther than the outer circumferential lip 115 of body 101. That is, the expanded section 113 serves as insertion-limiting flange that serves to limit the amount of insertion of the forward portion 110 of body 101 into the anus. The expanded section 113 includes a truncated conical surface 114, tapering from the outer circumferential lip 115 toward the rear edge of the cylindrical section 112.

Rearward portion 120 of body 101 comprises a forward section 121, a first arm 122 and a second arm 123. Forward section 121 of rearward portion 120 mates with rearward section 113 of forward portion 110, and may be joined thereto by, for example, adhesive. First arm 122 defines lumen 122a that receives connector 230 of inflation pump 200. Second arm 123 houses pressure relief valve 130 and indicator pin 140. Depending on the construction of the second arm 123, only part or all of the pressure relief valve 130 may be situated in the second arm 123. The pressure relief valve 130 may be any one of a number of commercial relief valves which open (i.e., allow the flow of air or another fluid therethrough) at specific pressures.

The pressure relief valve 130 has an inlet communicating with the interior space 100a and an outlet facing a head 141 of the indicator pin 140. The pressure relief valve 130 may have an existing construction that is designed to release air when a predetermined design pressure is present at the inlet.

The indicator pin 140 includes a head 141 that extends across the lumen 123a and a shaft 142 projecting rearward from the head 141 to a rear end of the second arm 123. The second arm 123 is constructed so that it retains the indicator pin 140 in connection therewith both before and after movement of the indicator pin 140 in response to release of pressure via the pressure relief valve 130 (see FIGS. 1 and 2). This may be achieved by providing a reduced cross-sectional area at the rear end of the lumen 123.

Inflation pump 200 comprises an elastomeric bulb 210, valves 221 and 222 and connector 230. Inflation pump 200 has a central portion 212 defining an interior space 212a receivable of air and is coupled to the rearward portion 120 of body 101. More specifically, connector 230 of inflation pump 200 is insertable into lumen 122a defined by the first arm 122 of the rearward portion 120 of body 101. Valve 221 at forward end 211 of inflation pump 200 is housed within the connector 230. Valve 222 is contained by the elastomeric bulb 210 at the rearward end 213 of inflation pump 200. Valves 221, 222 permit movement of air in one direction only, specifically in a direction from the rearward end 213 to the forward end 211 of inflation pump 200.

A central portion 212 of the elastomeric body 210 of inflation pump 200, between the valves 221 and 222, is compressible and when compressed, forces air from an interior space 212a, defined by the central portion 212 of the elastomeric bulb 210, through the valve 221 at the forward end 211 of the inflation pump 200, through the connector 230 and into conduit part 100. When the compressing force on the central portion 212 of the elastomeric bulb 210 is released, central portion 212 expands, and air flows into the space 212a through the valve 222 at the rearward end 213. Upon the next compression of the central portion 212 of the inflation pump 200, this air is then ejected through the connector 230 into conduit part 100. As such, a pumping action is obtained upon repeated compressions and releases of the central portion 212 of the inflation pump 200.

Figure 2:
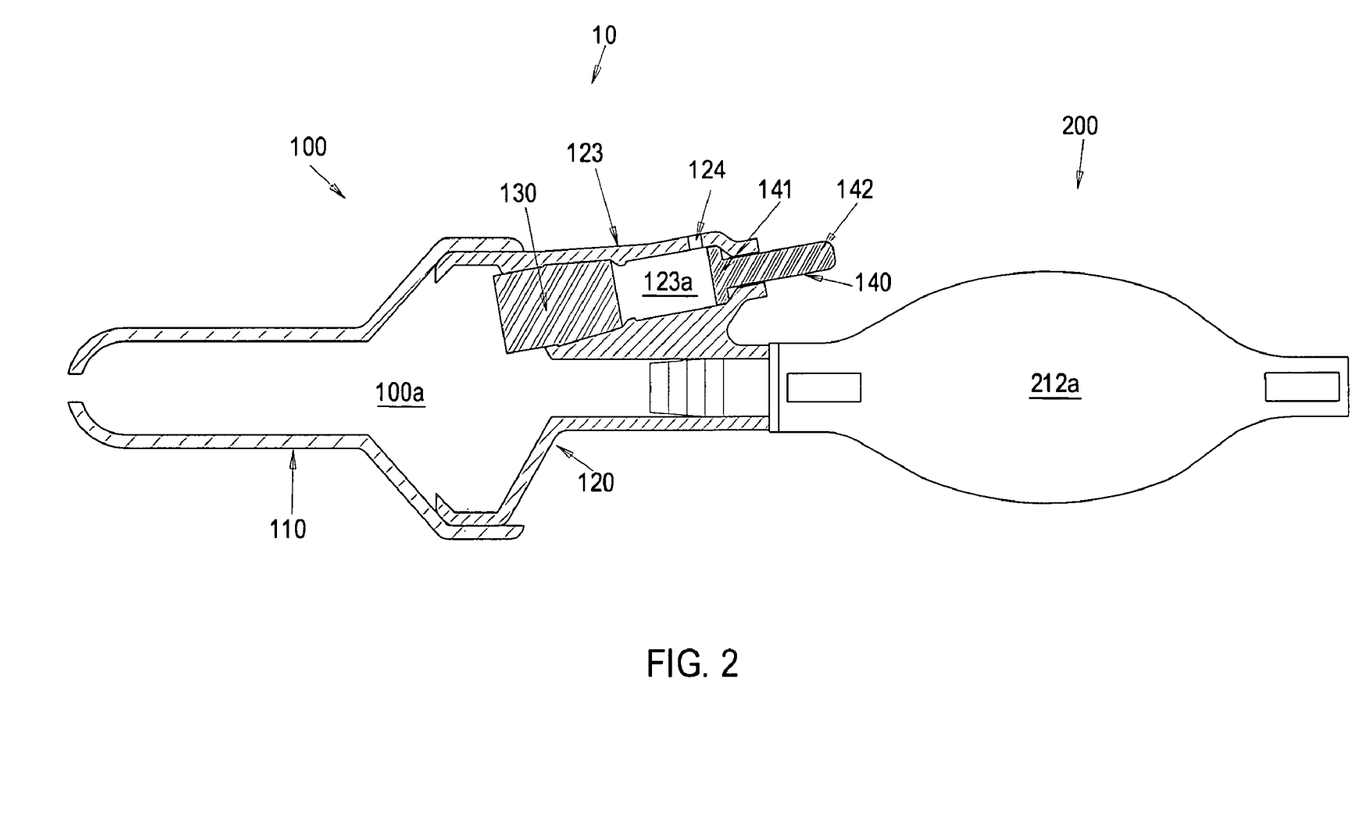
FIG. 2 is a partial longitudinal-section view of a colorectal anastomosis leak tester in accordance with the invention, with the indicator pin protruding in the ejected position.

When the air pressure in the rectum, which is the same as the pressure in the interior 100a of conduit part 100, reaches a specified pressure, air passes through pressure relief valve 130, presses against head 141 of indicator pin 140 and ejects shaft 142 of indicator pin 140 from lumen 123a of the second arm 123 of rearward portion 120 (see FIG. 2). The projecting indicator pin shaft 142 can be felt and/or seen by the surgeon, and thus signals to the surgeon that desired pressure within the rectum has been reached.

When the desired pressure is reached in the rectum, and air passes through valve 130 and indicator pin 140 is partially ejected, aperture 124 in the second arm 123 is brought into communication with pressure relief valve 130 because the head 141 of the indicator pin 140 has moved from a position between the aperture 124 and the pressure relief valve 130 (shown in FIG. 1) to a position between aperture 124 and the aperture at the rear end of the lumen 123a (shown in FIG. 2). As a result, the air in lumen 123a between the valve 130 and indicator pin head 141 is in flow communication with ambient air. Air from interior space 100a that passes through pressure relief valve 130 can then escape lumen 123a of body 101 through aperture 124. This pressure relief system prevents over-inflation of and damage to the rectal anastomosis.

In one exemplifying embodiment, the outer diameter of the cylindrical section 112 of forward portion 110 is approximately 0.63 inch, which has been determined to be suitable to allow it to be inserted into the anal canal of an anesthetized patient with ease, and to pass through all anastomoses normally formed in the rectum or anal canal. The largest diameter of the expanded portion 113, i.e., lip 115, in one embodiment has an approximate outer diameter of 2 inches, which is too large to enter the anal canal (without applying excessive force) and which thus abuts and seals the anal opening when pressed against the anal verge when the cylindrical section 112 is inserted completely into the anus. The expanded portion 113 thus serves to both limit the extent to which the anastomosis leak tester 10 is inserted into the rectum and seal the anal opening to prevent leakage of air around the anastomosis leak tester 10. Tubular section 122 of rearward portion 120 preferably has an inner diameter of approximately 0.375 inches, which accommodates the connector 230 of the inflation pump 200.

In one exemplifying use to test whether an anastomosis is leak-proof, the cylindrical section 112 of forward portion 110 of the anastomosis leak tester 10 is inserted into the anus of an anesthetized patient and the expanded portion 113 is pressed inward against the anus. The pelvis is filled with fluid and the bowel proximal to (above) the anastomosis is occluded with a clamp. Repeatedly compressing the inflation pump 200 distends the rectum with air. Air cannot escape from the anus because the conical expanded portion 113 occludes and seals the anal opening.

When the air pressure within the rectum exceeds a specified pressure, e.g., 30 cm water for open surgery and 50 cm water for laparoscopic surgery, air passes through pressure relief valve 130, presses against the head 141 of indicator pin 140 and ejects the narrow shaft 142 of indicator pin 140 from lumen 123a of the rearward portion 120 of body 101 (FIG. 2). When the surgeon feels and/or sees the presence of the ejected shaft 142 of the indicator pin 140, he knows that he has inflated the rectum to the desired pressure. When indicator pin shaft 142 is ejected, aperture 124 is brought into flow communication with pressure relief valve 130. If the surgeon continues to repetitively compress the inflation pump elastomeric bulb 210, air will be forced through pressure relief valve 130 and through aperture 124 into the ambient atmosphere, which prevents build up of excessive pressure in lumens 123a and 100a of conduit part 100, and the rectum.

When the rectum is sufficiently distended with air, and no air bubbles are seen in the pelvic fluid pool, it can be considered that the anastomosis is air tight. The anastomosis leak tester 10 is then removed out of engagement with the anus.

Figure 3:
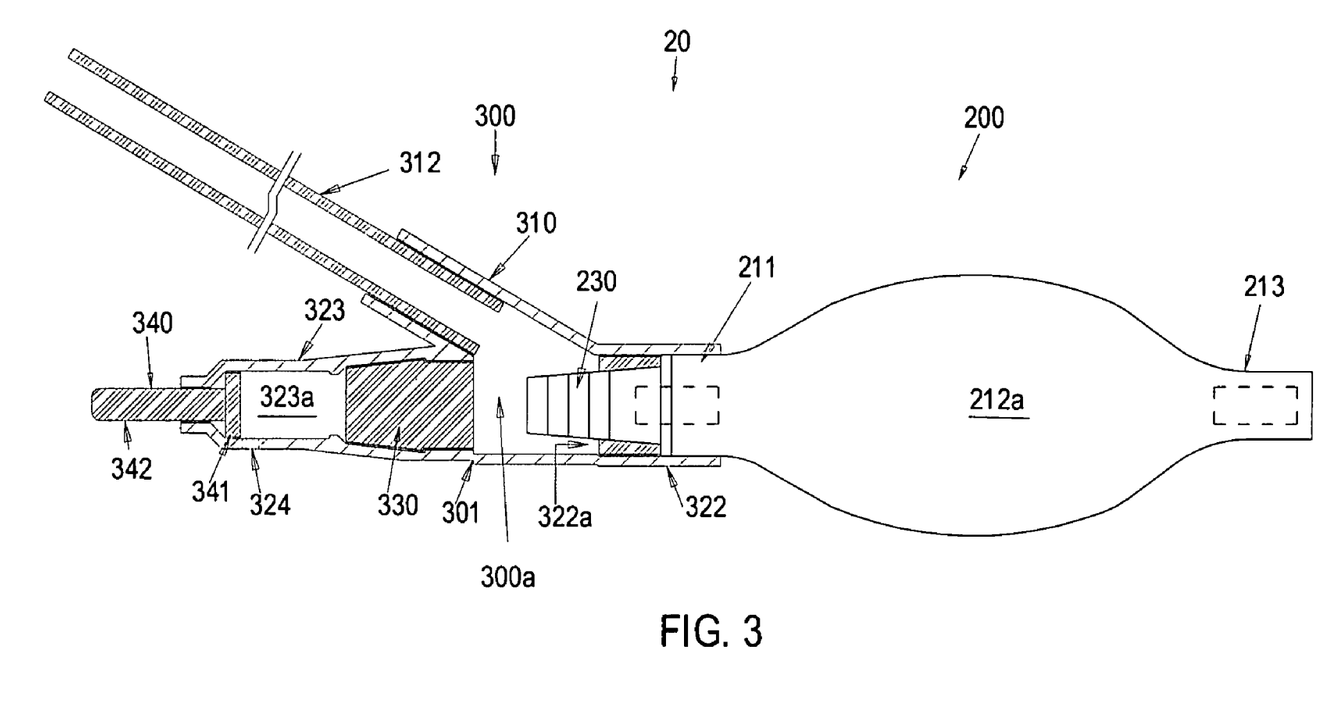
FIG. 3 is a partial longitudinal-section view of a gastrointestinal anastomosis leak tester in accordance with the invention, with the indicator pin protruding in the ejected position.

Another embodiment of the invention is seen in FIG. 3. Anastomosis leak tester 20 is a gastrointestinal anastomosis leak tester useful for testing gastroenteric and colorectal anastomoses. This embodiment comprises a substantially tubular conduit part 300 and an inflation pump 200. Conduit part 300 comprises a body 301 that houses a pressure relief valve 330 and an indicator pin 340.

Body 301, which defines interior space 300a of anastomosis leak tester 20 may be formed in one or multiple pieces. It may be made of elastomeric or rigid plastics, and fabricated using dip molding or injection molding techniques. Other plastic manufacturing methods can also be used.

Body 301 has side arm 310 that is adapted to mate with a tubing connector from a gastric tube by means of extension tube 312, rearward arm 322 that defines lumen 322a that receives connector 230 of inflation pump 200, and forward arm 323 that houses pressure relief valve 330 and indicator pin 340.

Inflation pump 200 may be identical in form and function to the inflation pump described above. Upon compressing central portion 212 of the inflation pump 200, air is directed through connector 230 into the conduit part 300 and through arm 310 and extension tube 312, through a tubing connector and through a gastric tube into a patient's stomach. When the air pressure in the patient's stomach, which is the same as the air pressure in the interior 300a of conduit part 300, reaches a specified pressure, air passes through pressure relief valve 330 and indicator pin shaft 342 is ejected from lumen 323a of conduit part 300. The projecting indicator pin shaft 342 can be seen and felt by the operator of the device, and thus signals to the operator that the desired pressure within the stomach has been reached.

When the desired pressure is reached in the stomach, and air passes through valve 330 and indicator pin 340 is ejected, aperture 324 is brought into communication with pressure relief valve 330 because the head 341 of the indicator pin 340 has moved from a position between the aperture 324 and the pressure relief valve 330 to a position between aperture 324 and the aperture at the forward end of the lumen 323a. Air from interior space 300a that passes through pressure relief valve 330 can then escape lumen 323a of conduit part 300 through aperture 324. This pressure relief system prevents over-inflation of and damage to the gastroenteric anastomosis.

In one exemplifying use to test whether a gastroenteric anastomosis is leak-proof, extension tube 312 of arm 310 of the anastomosis leak tester 20 receives a tubing connector connected to a gastric tube of an anesthetized patient whose gastroenteric anastomosis was just completed. The anastomosis is submersed in a clear fluid (saline or water) and the efferent limb of the anastomosis is occluded with a clamp. Repeated compressions of inflation pump 200 distends the stomach and anastomosis with air.

When the air pressure within the stomach exceeds a specified pressure, air passes through pressure relief valve 330, presses against the head 341 of indicator pin 340 and ejects the narrow shaft 342 from lumen 323a of conduit part 300. Once the operator (usually the anesthesiologist) sees or feels the presence of the ejected shaft 342 of the indicator pin 340, he would know that he has inflated the stomach to the desired pressure.

When indicator pin 340 is ejected, aperture 324 is brought into flow communication with pressure relief valve 330. If the operator continues to compress inflation pump 200, air will be forced through pressure relief valve 330 and through aperture 324 into the ambient atmosphere, which prevents build up of excessive pressure in lumens 323a and 300a of the conduit part 300, and the stomach.

When the stomach and anastomosis are sufficiently distended with air, and no air bubbles are seen in the fluid over the anastomosis, it can be considered that the anastomosis is air tight. The anastomosis leak tester 20 is then removed out of engagement with the gastric tube. The gastric tube is then aspirated to deflate the stomach.

The same gastrointestinal anastomosis leak tester can also be used to test colorectal anastomoses. In one exemplifying use to test whether a colorectal anastomosis is leak-proof, extension tube 312 of arm 310 of the anastomosis leak tester 20 is attached to the tubing port of a proctoscope. The proctoscope is inserted through the anus into the rectum of an anesthetized patient whose colorectal anastomosis was just completed. The anastomosis is submersed in a clear fluid (saline or water) and the bowel proximal to the anastomosis is occluded. Repeated compressions of inflation pump 200 distends the rectum and anastomosis with air.

When the air pressure within the rectum exceeds a specified pressure, air passes through pressure relief valve 330, presses against the head 341 of indicator pin 340 and ejects the narrow shaft 342 from lumen 323a of conduit part 300. When the surgeon sees and/or feels the presence of the ejected shaft 342 of the indicator pin 340, he knows that he has inflated the anastomosis to the desired pressure.

When indicator pin 340 is ejected, aperture 324 is brought into flow communication with pressure relief valve 330. If the surgeon continues to compress inflation pump 200, air will be forced through pressure relief valve 330 and through aperture 324 into the ambient atmosphere, which prevents build up of excessive pressure in lumens 323a and 300a of the conduit part 300, and the rectum.

When the rectum and anastomosis are sufficiently distended with air, and no air bubbles are seen in the fluid over the anastomosis, it can be considered that the anastomosis is air tight. The rectum can then be deflated by opening the gate of the proctoscope while the proctoscope is withdrawn.

The conduit parts 100, 300 described above exemplify two different constructions for introducing air into an internal body organ for the purpose of testing for leaks in an anastomosis in the organ. The common feature of the conduit parts 100, 300 is that the pressure of air in the interior space 100a, 300a of the conduit part 100, 300, respectively, is the same as the pressure in the internal body organ. Thus, more generally, the invention contemplates any form of a conduit part that is interposed between an inflation device and an inlet to a body organ, or a conduit or tube leading into the body organ, and that enables air from the interior space to be in communication with the body organ having the anastomosis being tested for leaks such that the air pressure in the interior space is the same as the air pressure in the body organ. By constructing the conduit part in this manner, the pressure in the interior space of the conduit part, which is limited by the pressure relief valve, functions to impose a limit on the pressure in the body organ thereby preventing it from being over-inflated.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention. For example, although a particular construction of the inflation pump 200 is described above, any inflation device that provides a unidirectional flow of air through an outlet that can be engaged with the body 100 or 300 may be used in accordance with the invention, whether manually actuated or automatically actuated. Further, although the inflation pump 200 includes a connector 230 that enters into a lumen 122a, 322a of the body 100, 300, it is conceivable that other mechanisms for connecting the outlet of the inflation pump 200 or other inflation device to an inlet of the body 100, 300 leading into the interior space therein 100a, 300a, which do not require a projecting male part of the inflation device and a receiving, female part of the body may be provided.

The entire contents of U.S. patent application Ser. Nos. 10/644,366 filed Sep. 17, 2003 and 11/444,783 filed Jun. 1, 2006, relating to anastomotic leak testing apparatus and methods, are incorporated by reference herein.

The invention claimed is:
1. A method for gastrointestinal anastomosis leak testing, comprising:
   providing an anastomosis leak tester comprising:
      a conduit part having an interior space, an opening communicating with the interior space that is adapted to communicate with a partially occluded gastrointesti- nal tract, an arm defining a lumen and an aperture defining a conduit between the lumen and the ambient atmosphere, a pressure relief valve communicating with the interior space, and a movable indicator pin separate from the pressure relief valve, the indicator pin being at least partly arranged in the lumen and relative to the pressure relief valve and the aperture such that the indicator pin has a first position in which the pressure relief valve is not in flow communication with the aperture and a second position in which the pressure relief valve is in flow communication with the aperture, the indicator pin occluding the lumen at a location between the aperture and the pressure relief valve to prevent the pressure relief valve from being in flow communication with the aperture when the indicator pin is in the first position, the indicator pin being arranged to be movable from the first position to the second position past the aperture upon outflow of air from the pressure relief valve to cause the pressure relief valve to be in flow communication with the aperture when the indicator pin is in the second position, submersing the anastomosis in fluid;

placing the conduit part in communication with the gastrointestinal tract and directing air into the interior space of the conduit part such that the air flows out of the interior space of the conduit part through the opening of the conduit part into the gastrointestinal tract to thereby distend the anastomosis;

continuing to direct air into the interior space of the conduit part until air is caused to pass through the pressure relief valve and moves the indicator pin from the first position to the second position thereby allowing air flow from the pressure relief valve to escape to the ambient atmosphere through the aperture and providing pressure release from the interior space of the conduit part; and then checking for anastomotic leaks based on the presence of air bubbles in the fluid around the anastomosis.

2. The method of claim 1, wherein the interior space of the conduit part is receivable of a connector from a gastric tube, rectal tube, or endoscope, further comprising:

connecting the conduit part to a gastric tube, rectal tube or endoscope.

3. The method of claim 1, wherein the conduit part has a forward tubular section having the opening communicating with the interior space, and an expanded section rearward of the forward tubular section, further comprising:

inserting the forward tubular section having the opening communicating with the interior space into the anus of a patient and pressing the expanded section against the anus to seal the anal opening;

filling the pelvis of the patient with fluid;

occluding the bowel above the anastomosis; and directing air into the interior space of the conduit part to cause air to flow into the interior space of the conduit part and out of the opening into the rectum to thereby distend the anastomosis.

4. The method of claim 1, wherein the indicator pin is configured relative to the arm to be retained partly within the arm after moving from the first position to the second position.

5. The method of claim 1, further comprising retaining part of the indicator pin in the arm after the indicator pin moves from the first position to the second position.

6. The method of claim 1, further comprising configuring the interior space of the conduit part to be receivable of a connector from a gastric tube, rectal tube, or endoscope.

7. The method of claim 1, further comprising arranging the pressure relief valve partly in the lumen.

8. The method of claim 1, further comprising providing the indicator pin with a head that extends across the lumen to thereby occlude the lumen and prevent the pressure relief valve from being in flow communication with the aperture when the indicator pin is in the first position.

9. The method of claim 8, further comprising providing the indicator pin with a shaft projecting rearward from the head, the aperture facing a part of the shaft when the indicator pin is in the first position.

10. The method of claim 8, further comprising positioning the head in the lumen and constructing the lumen such that the head is retained within the lumen as the indicator pin moves from the first position to the second position.

11. The method of claim 1, further comprising constructing the conduit part such that air can only be directed into the interior space of the conduit part through a lumen defined by an additional arm of the conduit part and that communicates with the interior space of the conduit part.

12. The method of claim 11, further comprising coupling an inflation pump to the lumen defined by the additional arm and actuating the inflation pump to thereby direct air into the interior space of the conduit part.

13. The method of claim 1, further comprising positioning the pressure relief valve and the indicator pin in the lumen with a space therebetween.

14. The method of claim 1, further comprising positioning the pressure relief valve partly in the interior space of the conduit part.

15. The method of claim 1, further comprising configuring the pressure relief valve to open and allow flow of air therethrough when air pressure in the interior space is at a specific pressure.

16. The method of claim 1, further comprising configuring the anastomosis leak tester such that the movement of the indicator pin from the first position to the second position provides a signal when air pressure within the gastrointestinal tract reaches a specified pressure and the pressure relief valve and the movement of the indicator pin from the first position to the second position prevents air pressure within the gastrointestinal tract from exceeding this specified pressure.

* * * * *